United States Patent
Borkovec et al.

(10) Patent No.: US 10,645,970 B2
(45) Date of Patent: May 12, 2020

(54) AEROSOL GENERATING COMPONENT FOR AN ELECTRONIC SMOKING DEVICE, ELECTRONIC SMOKING DEVICE AND METHOD FOR GENERATING AN INHALANT

(71) Applicant: Fontem Holdings 2 B.V., Amsterdam (NL)

(72) Inventors: Vaclav Borkovec, Hamburg (DE); Stefan Biel, Hamburg (DE); Diego Gonzalez, Amsterdam (NL)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 494 days.

(21) Appl. No.: 15/066,654

(22) Filed: Mar. 10, 2016

(65) Prior Publication Data

US 2016/0262457 A1    Sep. 15, 2016

(30) Foreign Application Priority Data

Mar. 13, 2015    (EP) .................. 15158978

(51) Int. Cl.
*A24F 47/00* (2020.01)
*A61M 11/00* (2006.01)
(Continued)

(52) U.S. Cl.
CPC ......... *A24F 47/008* (2013.01); *A61M 11/001* (2014.02); *A61M 11/005* (2013.01); *A61M 11/042* (2014.02); *A61M 15/002* (2014.02); *A61M 15/0003* (2014.02); *A61M 15/0085* (2013.01); *A61M 15/06* (2013.01); *H05B 3/0014* (2013.01); *A61M 2016/0021* (2013.01); *A61M 2205/3334* (2013.01);
(Continued)

(58) Field of Classification Search
None
See application file for complete search history.

(56) References Cited

U.S. PATENT DOCUMENTS

2002/0170566 A1    11/2002 Farr
2006/0201501 A1    9/2006 Morrison et al.
(Continued)

FOREIGN PATENT DOCUMENTS

CN    103974635 A    8/2014
CN    204169066 U    2/2015
(Continued)

OTHER PUBLICATIONS

European Patent Office, Examination Report issued in EP Patent Application No. 15158978.5 (dated Oct. 4, 2017).
(Continued)

*Primary Examiner* — Michael J Felton
*Assistant Examiner* — Katherine A Will
(74) *Attorney, Agent, or Firm* — Perkins Coie LLP; Kenneth H. Ohriner (57) ABSTRACT

The invention relates to aerosol generating components (40) for electronic smoking devices, to electronic smoking devices and in particular electronic cigarettes, and to methods for generating inhalants. In order to improve smoking experience by purposefully directing nicotine and flavor products, the invention provides that two aerosols with different particle sized are generated consecutively.

16 Claims, 4 Drawing Sheets

(51) Int. Cl.
*A61M 15/00* (2006.01)
*A61M 15/06* (2006.01)
*A61M 11/04* (2006.01)
*H05B 3/00* (2006.01)
A61M 16/00 (2006.01)
H05B 1/02 (2006.01)

(52) U.S. Cl.
CPC ............... *A61M 2205/3368* (2013.01); *A61M 2205/3653* (2013.01); *A61M 2205/8206* (2013.01); *H05B 1/0244* (2013.01)

(56) References Cited

U.S. PATENT DOCUMENTS

| | | |
|---|---|---|
| 2008/0029084 A1 | 2/2008 | Costantino et al. |
| 2008/0138398 A1 | 6/2008 | Gonda |
| 2008/0138399 A1 | 6/2008 | Gonda |
| 2008/0138423 A1 | 6/2008 | Gonda |
| 2013/0340775 A1 | 12/2013 | Juster et al. |
| 2014/0190496 A1 | 7/2014 | Wensley et al. |
| 2014/0353856 A1 | 12/2014 | Dubief |
| 2015/0196060 A1* | 7/2015 | Wensley ................ F22B 1/288 392/390 |
| 2015/0216237 A1* | 8/2015 | Wensley ............... A24F 47/008 131/273 |
| 2017/0251727 A1* | 9/2017 | Nielsen ................ A24F 47/008 |

FOREIGN PATENT DOCUMENTS

| | | |
|---|---|---|
| EP | 2460423 A1 | 6/2012 |
| WO | 2000/50111 | 8/2000 |
| WO | 2015112750 A1 | 7/2015 |
| WO | 2016033242 A1 | 3/2016 |
| WO | 2016040575 A1 | 3/2016 |

OTHER PUBLICATIONS

Intellectual Property Office, Combined Search and Examination Report under Sections 17 and 18(3) issued in GB Patent Application No. 1507671.4 (dated Jun. 30, 2015).

European Patent Office, European Search Report issued in EP Patent Application No. 15158978.5 (dated Oct. 2, 2015).

State Intellectual Propertyoffice, First Office Action for Chinese Application No. 20161044162.1; dated Jul. 23, 2019; 18 pages.

* cited by examiner

AEROSOL GENERATING COMPONENT FOR AN ELECTRONIC SMOKING DEVICE, ELECTRONIC SMOKING DEVICE AND METHOD FOR GENERATING AN INHALANT

PRIORITY CLAIM

This application claims priority to EP Patent Application No. 15158978.5, filed Mar. 13, 2015, and now pending.

BACKGROUND OF THE INVENTION

An electronic smoking device, such as an electronic cigarette (e-cigarette), usually has a housing accommodating an electric power source (e.g. a single use battery or a rechargeable battery), and an electrically operable atomizer. The atomizer vaporizes or atomizes liquid supplied from a reservoir and provides vaporized or atomized liquid as an aerosol. Control electronics control the activation of the atomizer. In many electronic cigarettes, an airflow sensor is provided within the electronic smoking device which detects a user puffing on the device (e.g. by sensing an underpressure or an air flow pattern through the device). The airflow sensor indicates or signals the puff to the control electronics. Alternatively, a button may be used to switch on the electronic smoking device to generate a puff of flavor. When a puff is detected, the control electronics supplies electrical power to the atomizer thereby creating vaporized liquid as an aerosol.

It is desirable to provide two different aerosols that can be inhaled, the aerosols for example comprising a flavor product and/or a nicotine product.

Flavor products preferably comprise flavored materials added to a liquid. Flavored materials are for example esters, such as isoamyl acetate, linalyl acetate, isoamyl propionate, linalyl butyrate and the like or natural essential oils as plant essential oils, such as spearmint, peppermint, cassia, jasmine and the like or animal essential oils, such as musk, amber, civet, castor and the like or simple flavoring materials, such as anethole, limonene, linalool, eugenol and the like or hydrophilic flavour components such as a leaf tobacco extract or natural plant flavoring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavored materials as mentioned above into new flavored materials. Moreover, it is possible to adsorb any flavor onto a solid material and to use this material as flavored material within an electronic smoking device according to the present invention.

SUMMARY OF THE INVENTION

In accordance with one aspect of the present invention there is provided an aerosol generating component for an electronic smoking device. The aerosol generating component may have a single atomizer. The atomizer is adapted to consecutively generate two aerosols with different particle sizes. Furthermore, in accordance with another aspect of the present invention, there is provided an electronic smoking device comprising an aerosol generating component according to the invention. Moreover, in accordance with yet another aspect of the present invention, there is provided a method for generating an inhalant to a user. In order to generate the inhalant, a first aerosol with a first particle size and a second aerosol with a second particle size are consecutively generated. The first particle size differs from the second particle size.

An advantage of the aerosol generating component according to the present invention is that the particle size can be preselected for chosen materials to be inhaled, such that the materials can be transported to desired locations within the respiratory system of the user of the smoking device.

Figure 1:
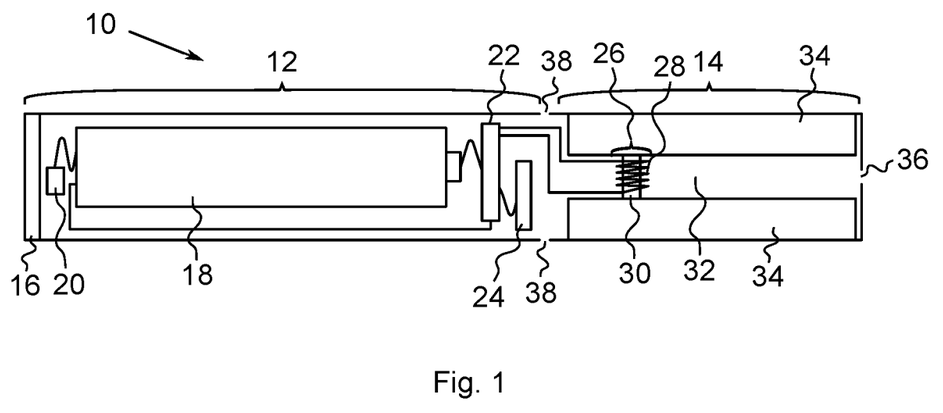

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views:

FIG. 1 is a schematic cross-sectional illustration of an exemplary e-cigarette;

FIG. 2 is a schematic view of an aerosol generating component according a preferred embodiment of the invention;

FIG. 3 is another schematic view of the aerosol generating component according to the embodiment of FIG. 2;

FIG. 4 is a schematic view of a first preferred embodiment of a gas inlet element according to the embodiment of FIG. 3;

FIG. 5 is a schematic view of second preferred embodiment of a gas inlet element according to the embodiment of FIG. 3;

FIG. 6 is a schematic cross-sectional illustration of an e-cigarette according a preferred embodiment of the invention; and FIG. 7 is a schematic view of an exemplary embodiment of a method according to the invention.

DESCRIPTION OF THE PREFERRED EMBODIMENTS

Prior to describing an embodiment of the present invention, the basic structure of an e-cigarette will first be described with reference to FIG. 1 which is a schematic cross-sectional illustration of an exemplary e-cigarette.

As is shown in FIG. 1, an e-cigarette 10 ordinarily comprises a cylindrical housing having a main body 12 and a mouthpiece portion 14. Together the main body 12 and the mouthpiece portion 14 form a cylindrical tube which is approximately the same size and shape as a conventional cigarette. The main body 12 and mouthpiece 14 are typically made of steel or hardwearing plastic and act to provide a housing to contain the operative elements of the e-cigarette 10. The main body 12 and a mouthpiece portion 14 may be configured to fit together by means of a friction push fit. Alternatively in some embodiments a screw fit may be provided enabling the main body 12 and mouthpiece portion 14 to be attached to one another. Alternatively in some e-cigarettes the main body 12 and mouthpiece portion 14 may be parts of a single integrally formed tube.

An end cap 16 is provided at the end of the main body 12 remote from the mouthpiece portion 14 enclosing that end of the main body 12. The end cap 16 is typically made from translucent plastic.

A battery 18 is provided within the central cavity enclosed by the main body 12. Also contained within the central cavity defined by the main body 12 are a light emitting diode (LED) 20, control electronics 22 and an airflow sensor 24. The battery 18 is electrically connected to the LED 20 and the control electronics 22 and the airflow sensor 24 is connected to the control electronics 22. In this example the LED 20 is provided at one end of the main body 12, adjacent to the end cap 16 and the control electronics 22 and airflow sensor 24 are provided in the central cavity at the other end of the battery 18 adjacent the mouth piece portion 14.

The airflow sensor 24 acts as a puff detector, detecting a user puffing or sucking on the mouthpiece portion 14 of the e-cigarette 10. The airflow sensor 24 can be any suitable sensor for detecting changes in airflow or air pressure, such as a microphone switch including a deformable membrane which is caused to move by variations in air pressure.

The control electronics 22 are also connected to an atomizer 26 which in this illustrative example comprises a heating coil 28 which is wrapped around a wick 30 which extends across a central passage 32 provided in the mouthpiece portion 14 of the e-cigarette 10. The dimensions of the central passage 32, the wick 30 and the heating coil 28 are such that the wick 30 and heating coil 28 do not completely block the central passage 32 but rather an air gap is provided either side of the heating coil 28 enabling air to flow past the heating coil 28 and wick 30.

The central passage 32 is surrounded by a cylindrical liquid store 34 with the ends of the wick 30 abutting or extending into the liquid store 34. The wick 30 comprises a porous material such as a bundle of fiberglass fibers such that liquid present in the liquid store 34 is drawn by capillary action from the ends of the wick 30 towards the central portion of the wick 30 encircled by the heating coil 28.

In some embodiments the liquid store 34 will comprise wadding soaked in liquid which encircles the central passage 32 with the ends of the wick 30 abutting the wadding. In other embodiments the liquid store 34 may comprise a toroidal cavity arranged to be filled with liquid to be vaporized with the toroidal cavity enclosed by walls and with the ends of the wick 30 extending into the toroidal cavity.

An air inhalation port 36 is provided at the end of the mouthpiece portion 14 remote from main body 12 of the e-cigarette 10 and a pair of air inlets 38 are provided in the housing at the intersection between the main body 12 and the mouthpiece portion 14 adjacent the airflow sensor 24 with the central passage 32 within the mouthpiece portion 14 of the e-cigarette 10 extending from adjacent the air inlets 38 past the wick 30 and heating coil 28 to the air inhalation port 36.

In use, a user sucks on the mouthpiece portion 14 of the e-cigarette 10. This causes air to be drawn into the e-cigarette 10 via the air inlets 38 and to be drawn up via the central passage 32 towards the air inhalation port 36. The change in air pressure which arises is detected by the airflow sensor 24 which generates an electrical signal that is passed to the control electronics 22. In response to the signal, the control electronics 22 then proceed to activate the heating coil 28 which causes liquid present in the wick 30 to be vaporized creating an aerosol (which may comprise gaseous and liquid components) within the central passage 32. As the user continues to suck on the mouthpiece portion 14 of the e-cigarette 10, this aerosol is drawn up the central passage 32 and inhaled by the user sucking on the e-cigarette 10. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol more liquid is drawn into the wick 30 from the liquid store 34 by capillary action and thus is available to be converted into an aerosol through subsequent activation of the heating coil 28.

In some e-cigarettes, the e-cigarette 10 is intended to be disposable and the electric power in the battery 18 is intended to be sufficient to vaporize the liquid contained within the liquid store 34 after which the e-cigarette 10 is thrown away. In other embodiments the battery 18 is rechargeable and a means is provided to replenish the liquid supply. In the cases where the liquid store 34 is a toroidal cavity, this may be achieved by providing a refill port and refilling the cavity with liquid via the refill port. In other embodiments the mouthpiece portion 14 of the e-cigarette 10 is detachable from the main body 12 and a new mouthpiece portion 14 can be fitted with a new liquid store 34 thereby replenishing the supply of liquid. In some cases, replacing the liquid store 34 may involve replacement of the heating coil 28 and the wick 30 along with the replacement of the liquid store 34.

In some cases the new liquid store 34 may be in the form of a cartridge. In some such embodiments the cartridge may be provided with a central passage 32 through which a user inhales aerosol generated by the e-cigarette. In other embodiments, rather than inhaling aerosol via a central passage 32, the cartridge may be such to block the central portion of the e-cigarette 10 and generated aerosol may be directed around the exterior of the cartridge 32 to an air inhalation port 36 for inhalation.

It will also be appreciated that although the above description is illustrative of the structure and function of a typical e-cigarette 10, variations also exist. Thus for example in some e-cigarettes the LED 20 is omitted. In some e-cigarettes, the airflow sensor 24 may be placed adjacent the end cap 16 of the e-cigarette rather than in the middle of the e-cigarette as illustrated. Similarly, in some e-cigarettes, the air inlets 38 may be placed at the distal end of the main body 16 of the e-cigarette 10 remote from the mouthpiece portion 14. In some e-cigarettes the airflow sensor 24 is omitted and instead a button is provided which enables a user to activate the e-cigarette manually rather than in response to the detection of a change in air flow or air pressure. Also in some e-cigarettes the constitution of the atomizer may be changed. Thus for example rather than being constituted by a wick 30 surrounded by a heating coil 28 other configurations may be used such as providing a heating coil in a cavity in the interior of a porous body soaked in liquid for atomization and generating an aerosol by evaporating the liquid within the porous body either by virtue of the activation of the coil heating the porous body or alternatively by virtue of the heated air being passed over or through the porous body. Further in some embodiments rather than generating an aerosol through heating liquid within a wick 30 an aerosol might be generated using a piezoelectric atomizer to create an aerosol for inhalation either in combination or in the absence of a heater.

Figure 2:
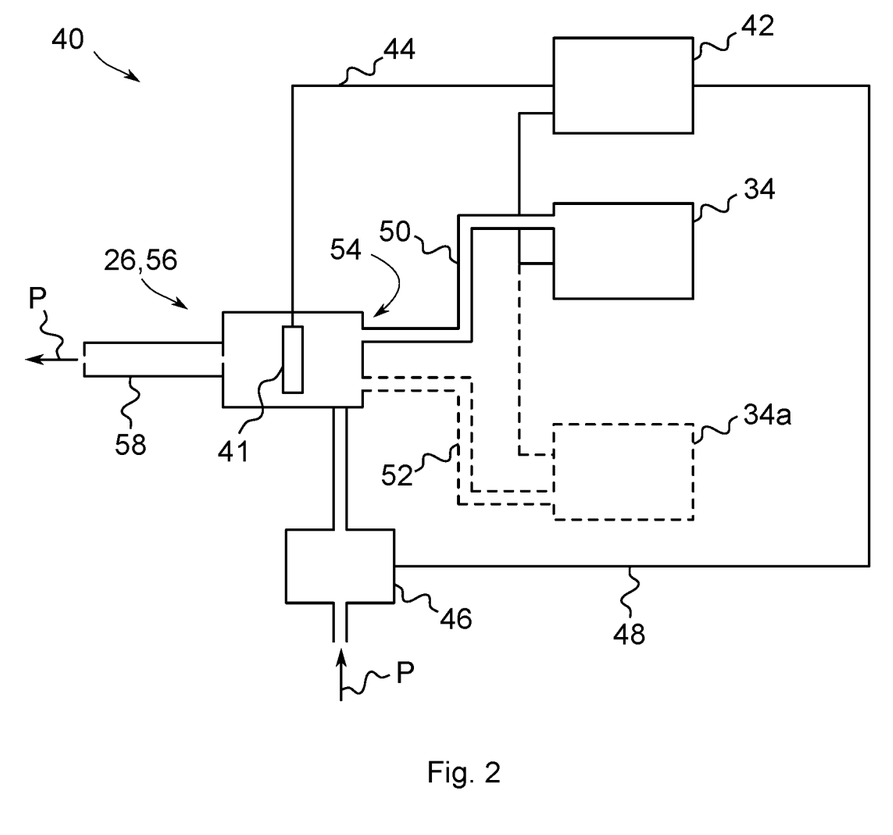

FIG. 2 shows a schematic view of an aerosol generating component 40 according to the present invention. The aerosol generating component 40 is adapted to consecutively generate two aerosols, a particle size of a first of the aerosols differing from a particle size from a second of the aerosols. The particle sizes can be easily measured, for example by generating the two aerosols and by measuring the particle sizes of these two aerosols. For example, the same materials may be used to generate the two aerosols for controlling that the aerosol generating component 40 is adapted to generate two aerosols with different particle sizes. Furthermore, in case different materials are to be atomized in order to generate the two aerosols for inhalation with the electronic smoking device, e.g. the e-cigarette 10, the particle sizes of these aerosols can, again, easily be determined, for example by known particle size measurement methods.

The aerosol generating component 40 comprises the atomizer 26 that is adapted to generate the aerosols by atomizing or vaporizing materials to be inhaled. For example, the atomizer 26 may have different predetermined operational states, which result in the different particle sizes of the aerosols. The atomizer 26 comprises an atomizing element 41, which atomizes and for example vaporizes the materials to be inhaled. By providing such an atomizer 26 each of aerosols from the material or the materials to be inhaled can be easily provided without the need for a second atomizer, which would require additional installation space. A flow path P interconnecting the air inhalation port 36 and at least one air inlet 38 extends through the atomizer 26.

The aerosol generating component 40 comprises an electronic control unit 42 for controlling process properties of the atomizer 26. In order to be able to control process properties of the atomizer 26, the control unit 42 is connected at least to the atomizer 26, e.g. in a signal transmitting manner, for example by at least one signal conductor 44. The control unit 42 comprises electronics for controlling at least the process properties of the atomizer 26.

Furthermore, the aerosol generating component 40 may comprise an air supply control unit 46. For supplying air to the atomizer 26, the air supply control unit 46 is adapted such that the flow, amount or quantity of air provided to the atomizer 26 is changeable. Along the flow path P, the air supply control unit 46 is arranged upstream of the atomizer 26. In case the aerosol generating component 40 is part of the electronic smoking device 10, the air supply control unit 46 interconnects at least one air inlet 38 and the atomizer 26.

The air supply control unit 46 is adjustable, such that the flow, amount or quantity of the air supplied to the atomizer 26 can be changed. For example, the air supply control unit 46 may be adapted such that a user of the electronic smoking device 10 can select flows, amounts or quantities of air to be supplied to the atomizer 26 for generating the aerosols. Alternatively, information concerning flows, amounts or quantities of air to be supplied to the atomizer 26 may be provided, e.g. by the smoking device 10 or by the liquid store 34, for example a container, comprising the material to be inhaled.

The aerosol generating component 40 may be adapted within the electronic smoking device 10 to adjust flows, amounts or quantities of air to be supplied to the atomizer 26, such that one of the aerosols is not at all mixed, i.e. diluted, with air to form the inhalant. Alternatively or additionally, mixing ratios of 25/75, 50/50, 75/25 and/or 100/0 or ratios therebetween can be predefined. Furthermore, mixing ratios of the aerosols with air may be selectable to mixing ratios of 25/75, 50/50, 75/25 and/or 100/0 or ratios therebetween by the air supply control unit 46. In order to be able to change the mixing ratio, the control unit 42 may be connected to the air supply control unit 46, preferably in a control signal transmitting manner, for example by another signal conductor 48.

The atomizer 26 is connected to the liquid store 34 and an optionally provided liquid store 34*a* in a liquid conducting manner, for example by liquid conductors 50, 52, which may be provided as pipes or tubes. In particular, the liquid stores 34, 34*a* are connected to an input side 54 of the atomizer 26. An output side 56 of the atomizer 26 is connected to the mouth piece portion 14 of the electronic smoking device 10, if the aerosol generating component 40 is part of the electronic smoking device 10. To be able to connect the aerosol generating component 40 with the mouth piece portion 14, the aerosol generating component 40 comprises an optional adapter or fitting 58, which is connected to the output side 56 of the atomizer 26 in an aerosol conductive manner.

Figure 3:
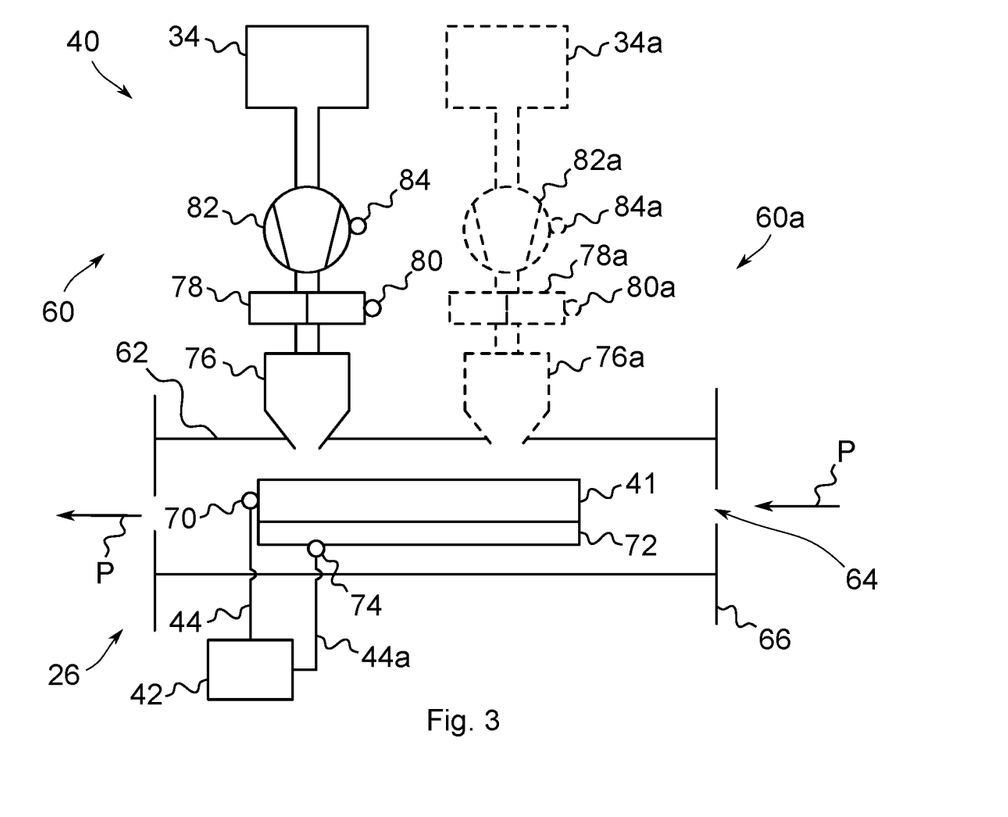
Figure 4:
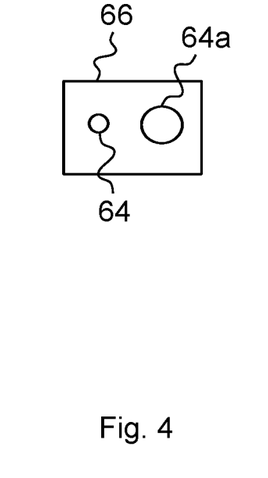
Figure 5:
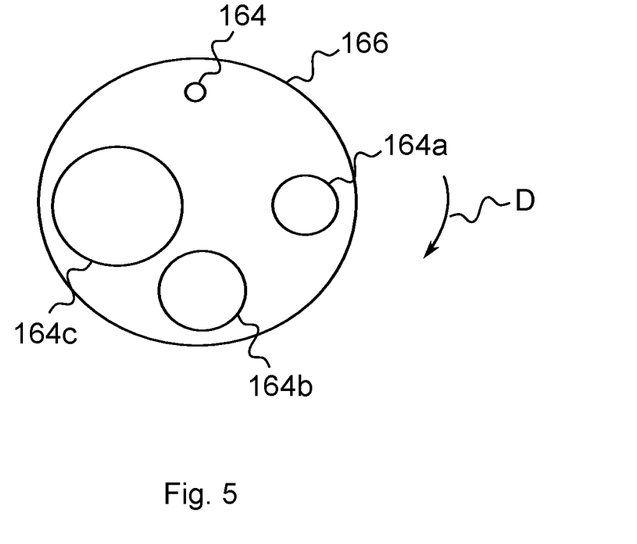
Figure 6:
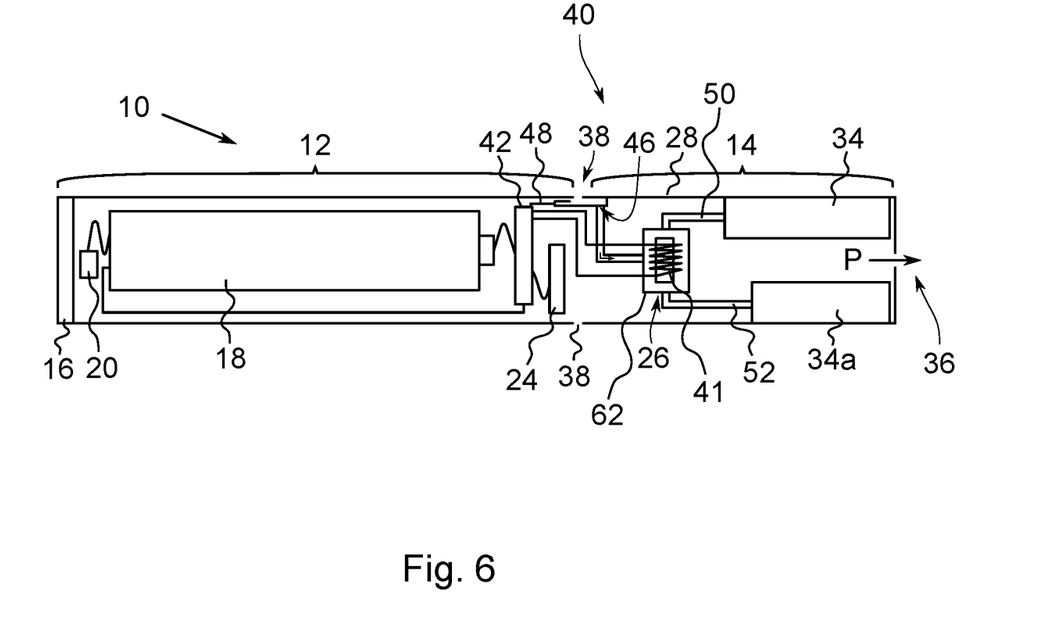
Figure 7:
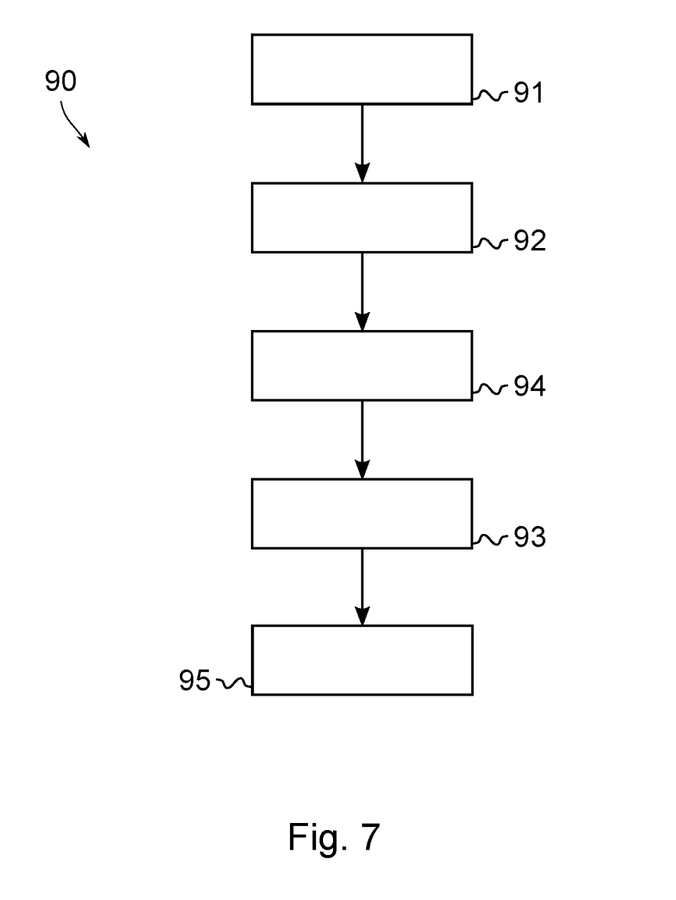

FIG. 3 shows a schematic cross-sectional view of the aerosol generating component 40 of FIG. 2 and with a liquid supply unit 60, as well as with an optional liquid supply unit 60*a*. The optional liquid supply 60*a* may have the same basic structure as the liquid supply 60, but may differ from the liquid supply 60 in that it is adapted to generate a different flow of liquid.

The atomizer 26 comprises a mixing chamber 62 for mixing atomized material with gas, the gas preferably being ambient air and led into the mixing chamber 62 via the flow path P.

In order to consecutively generate the aerosols with different particle sizes, different gas streams, e.g. with different forms, directions and/or flow rates, may be consecutively supplied into the mixing chamber 62. Due to the flow characteristics of the gas, e.g. represented by the Reynolds-number, which may be mainly determined by the form and/or the dimension of an inlet opening 64 of the mixing chambers 62, an effective influence of the particle sizes is achieved. The gas, namely, influences the particle size, as e.g. a higher flow may result in a turbulent gas stream, which may cause a higher interaction between particles, again resulting in larger particles. Cooling the atomized material, for example by mixing the atomized material with gas, i.e. gaseous dilution, influences the condensation of atomized material into liquid droplets, i.e. the particles, which influences the particle size, too. Hence, the particle sizes of the aerosols can be preselected in hardware by the form or dimensions of the inlet opening 64. High airflow without low or no turbulence results in high dilution, which reduces the interaction between particles and stops them growing in size. Low airflow results in low dilution, which, in addition or alternative to the high turbulence, increases the probability of the particles growing.

According to an embodiment, the predefined size of the particles in the aerosol generated with the atomizer 26 is changeable. Hence, in order to be able to change the size of the particles, the inlet opening 64 of the atomizer 26 is changeable.

The size of the respective inlet opening 64 may be selectable by the user and may be changeable manually. Alternatively or additionally, the size change of the inlet opening 64 may be predetermined, for example by the smoking device 10. In particular, an inner diameter of the inlet opening 64 may be changeable, such that different amounts of gas can be led into the mixing chamber 62.

The inlet opening 64 may be formed by an iris diaphragm with a variable inner diameter. Alternatively or additionally, the atomizer 26 comprises a gas inlet element 66 which comprises the inlet opening 64. The gas inlet element 66 may be exchangeable against another gas inlet element 66, which may have another inlet opening 64 that is differently dimensioned.

Alternatively or additionally, the gas inlet element 66 may be provided with at least two inlet openings 64 communicating with each other, i.e. in a gas conductive contact, with an inner volume of the mixing chamber 62 as desired, i.e. one or the other or even both of the inlet openings 64, for example at choice of the user or according to a predetermined information provided by the smoking device 10. In case two inlet openings 64 are gas conductively connected to the inner volume of the mixing chamber 62, the combined surface of the inlet openings 64 defines a surface through which gas can be led into the mixing chamber 62. Hence, even if the gas inlet element 66 comprises at least two inlet openings 64 with identical dimensions, the gas stream into the mixing chamber 62 can be easily changed.

The gas inlet element 66 may be formed as a plate that is moveable with respect to the mixing chamber 62 or even exchangeable. Alternatively, the inlet openings 64 may be formed by gas ducts of the gas inlet element 66, the gas inlet element 66 preferably being moveable with respect to the mixing chamber 62 or even exchangeable.

The inlet openings 64 may separately from each other be connected with the environment of the aerosol generating component 40 or even of the electronic smoking device 10, in order to decouple gas or air streams led through the inlet opening 64.

The atomizer 26 comprises the atomizing element 41 for atomizing material for the aerosols. In order to better influence the particle size independent of the dimension of the inlet opening 64 or in addition to the dimensioning of the inlet opening 64, the atomizing element 41 of the atomizer 26 is preferably adapted to allow for generation of the first aerosol, and to allow for generation of the second aerosol. The operation properties or parameters of the atomizing element 68 may be changeable in order to be able to adjust the particle size. The operation properties or parameters may be electrical power or frequency of an operation power fed to the atomizing element 68.

The atomizing element 41 may be provided with a control contact 70, such that the respective atomizing element 68 can be connected to the control unit 42, preferably in a control signal transmitting manner.

The atomizing element 41 may be formed as an ultrasonic atomizer, e.g. with a piezo electric elements that generates ultrasound when operated, which may be differently operated. For example, the ultrasonic atomizer may be operated at different frequencies and/or amplitudes in order to generate the different particle sizes.

Alternatively, the atomizing element 68 is a heating element for atomizing materials for the aerosols by evaporation, the heating element being adapted to allow for generation of the aerosols with the different particle sizes. For example, the heating element may have two predetermined operation temperatures different from each other. Possible predefined operating temperatures of the heating element are between 130° C. and 300° C., for example around 220° C.

For example, the heating element comprises the heating coil 28. The heating element may further comprise the wick 30, which prevents liquid materials to be atomized from forming drops which drop off of the heating element. Alternatively, the heating element may not comprise the wick 30 and can, instead, have a geometry which acts like a wick material to keep the liquid in contact with the wire of the coil 28 through cohesive properties of the liquid.

Different temperatures influence the particle size. For example, warmer atomized materials tend to have larger particle sizes than colder atomized materials, as an increase of the temperature results in an increased particle interaction and agglomeration of the particles, resulting in larger particles.

Higher power delivery results in a higher temperature, which increases the rate of vaporization, such that larger particles are created. Lower power delivery results in a lower temperature, which results in smaller particles. The temperature achieved in the material to be atomized and in particular to be vaporized can also be controlled by mass of the material that impinges the atomizing elements.

The atomizer 26 of the exemplary embodiment optionally comprises a temperature sensor 72 for sensing the temperature of the heating element, the temperature sensor 72 being connected to the control unit 42, for example in a sensor signal transmitting manner. In order to be connectable to the control unit 42, the temperature sensor 72 preferably comprises a signal contact 74 that is connected with or connectable to the control unit 42 via a signal conductor 44*a*. A temperature sensor converts a temperature into a signal that is representative for the temperature. Exemplary temperature sensors are negative or positive temperature coefficient resistors. The temperature of the heating element can be controlled by the control unit 42, such that the temperature of the heating element is within ±10° C. or even within ±1° C. of the respective predetermined operation temperature.

Due to the temperature sensor 72, the temperature of the atomizing element 68 can be controlled and even influenced by the control unit 42, such that the atomizing element 68 is operated at the respective predetermined operation temperature, which may be preset in the control unit 42. The predetermined operation state of the respective atomizing element 68, in particular the predetermined operation temperature, may be controlled during atomizing the material to be atomized, such that for example the temperature of the atomizing element 68 decreases less due to the atomizing process.

As explained above, the quantity of the material to be atomized influences the temperature of the atomized materials due to the different thermal mass to which the respective atomizing element 68 is exposed. Thus, due to the temperature sensor 72, the temperature of the heating element can be influenced and for example be maintained within a preset temperature range during evaporation.

Hence, the predetermined operation temperatures may be stored or storable or may be represented by data or rules stored in the control unit 42 and/or the liquid store 34. In case different materials shall be atomized at the user's selection, the predetermined operation temperatures can depend on the material to be atomized and may be selected by the user, provided by the smoking device 10 or by information provided with the materials to be inhaled.

In order to provide the material to be atomized, the atomizer 26 comprises the liquid supply unit 60 and optionally the liquid supply unit 60*a* supplying the material to be atomized to the atomizing element 68. The liquid supply 60 of the atomizer 26 may be adapted to allow for generation of the first aerosol and the liquid supply 60*a* may be adapted to allow for generation of the second aerosol. Alternatively, the liquid supply unit 60 may be adapted to allow for generation of the first aerosol and, after that, for the second aerosol.

In particular, the liquid supply unit 60 may be adapted to supply a first quantity of the material to be inhaled in one puff, and the optional liquid supply unit 60*a* may be adapted to supply a second quantity of the material to be inhaled in one puff, the second quantity differing from the first quantity. For example, at least one of the liquid supply units 60, 60*a* is adapted to supply quantities between 0.05 µl to 5 µl, for example between 0.1 µl and 2 µl, in particular of 1 µl. The other one of the liquid supply units 60, 60*a* may be adapted to supply a different quantity than the one of the liquid supply units 60, 60*a*, the quantities being between 0.05 µl to 5 µl, for example between 0.1 µl and 2 µl, in particular of 1

μl. Alternatively, in case only one liquid supply unit 60 is provided, the quantity supplied may be changed during the supply procedure, e.g. during the puff.

The control unit 42 is connected to at least one and in particular to both of the liquid supply units 60, 60a, for example in a control signal transmitting manner. The control unit 42 may be adapted to control the quantity of the material to be atomized and subsequently inhaled, that is supplied to the atomizing element 68.

Alternatively or additionally, the control unit 42 can be adapted to activate at least one of the liquid supply units 60, 60a after the atomizing element 68 has reached a predetermined operation state. For example, the control unit 42 may activate one or both of the liquid supply units 60, 60*a* after the heating element has reached the predetermined operation temperature.

The liquid supply units 60, 60*a* may each comprise a nozzle 76, 76*a* that is directed towards the respective atomizing element 68. For example, the nozzle 76, 76*a* is arranged above the atomizing element 68 in a direction of gravity, if the electronic smoking device 10 is held in a predefined smoking position. The nozzle 76, 76*a* is preferably a small orifice, which is dimensioned to dispense and e.g. spray liquid materials to be atomized onto the atomizing element 68. Via the nozzle 76, 76*a*, material to be atomized, in particular liquids, are dispensed onto the atomizing element 68 in an extensive manner such that the atomizing element 68 is uniformly coverable with the material to be atomized. In many applications, gravity forces are negligible relative to fluid forces, so that the arrangement of the nozzle relative to gravity is not relevant.

Preferably, the nozzles 76, 76*a* are different nozzles 76, 76*a*, which may be differently dimensioned. Alternatively or additionally, the distance between the nozzle 76 and the atomizing element 68 may be different to the distance between the nozzle 76*a* and the atomizing element 68 in order to achieve that aerosols with different particle sizes are generated.

A valve 78, 78*a* may be arranged upstream of the nozzle 76, 76*a*, the valve 78, 78*a* adjusting the flow of material to be atomized to the nozzle 76, 76*a*. The valve 78, 78*a* may be provided with a control contact 80, 80*a* that may be connectable or connected to the control unit 42, such that supply of the material to be atomized to the nozzle 76, 76*a* can be controlled by the control unit 42.

A pump 82, 82*a* for transporting the material to be atomized via the optional valve 78, 78*a* towards the nozzle 76, 76*a* may be provided. The pump 82, 82*a* may be manually actuatable by the user, e.g. when the user presses the manual actuator. Alternatively, the pump 82, 82*a* may be electrically driven. In order to be able to control the pump 82, 82*a*, the pump 82, 82*a* may be provided with a control contact 84, 84*a* that can be connected to the control unit 42. In particular in case the control unit 42 controls the pump 82, 82*a*, the valve 78, 78*a* is optional in order to control the flow of material to be atomized towards the nozzle 76, 76*a*. Yet, the valve 78, 78*a* may be provided, for example in case the pump 82, 82*a* is manually driven by the user. For example, the pump 82, 82*a* may be a displacement or a micro-pump, for example a peristaltic pump. The pump 82, 82*a* could also be puff actuated, such that the underpressure caused by a puff drives the pump.

Upstream of the pump 82, 82*a*, the liquid store 34, 34*a* for the material to be atomized is arranged according to the exemplary embodiment. The liquid store 34, 34*a* may be a fillable or a refillable or an exchangeable or even a disposable tank, cartridge, container or capsule. In case the liquid store 34, 34*a* is exchangeable or disposable, information representing a desired particle size or atomization parameters may be provided by the liquid store 34, 34*a*

A gas or ambient air temperature sensor may be provided to determine the temperature of the gas ambient air outside of the aerosol generating component 40 or of the electronic smoking device 10. The ambient air temperature sensor, which is not shown in the Figures for the sake of simplicity, may be connected to the control unit 42, preferably in a sensor signal transmitting manner. The control unit 42 may control the atomizing element 68 and/or at least one or even both of the liquid supply units 60, 60*a* in dependence of the ambient temperature in order to influence the particle sizes.

Alternatively or additionally, based on the sensor signal from the temperature sensor 72, the control unit 42 may determine the ambient temperature by measuring the period necessary for reaching the predetermined operation temperature for the atomizing element 68. In case the period is either longer or shorter than expected, the control unit 42 can determine that the ambient temperature is either lower or higher than expected and can adapt the parameters of the atomizing element 68 and/or at least one or even both of the liquid supply units 60, 60*a* accordingly. For example, in case the period is shorter, the control unit 42 may determine that the ambient temperature is higher, and can adjust the operation parameters of the atomizing element 68 and/or at least one or even both of the liquid supply units 60, 60*a*, such that less energy is provided to the atomizing element 68 and/or less material to be atomized is provided by at least one or even both of the liquid supply units 60, 60*a*. Optionally, the atomizer 26 may comprise a pre-heating element for preheating the gas, e.g. the ambient air, before it is led into the mixing chamber 62 such that the gas led into the mixing chamber 62 has a constant temperature that is independent of the temperature outside of the aerosol generating component 40 or of the electronic smoking device 10.

FIG. 4 schematically shows a first exemplary embodiment of a gas inlet element 66. The gas inlet element 66 of the exemplary embodiment of FIG. 4 is formed with two inlet openings 64, 64*a*, which are differently dimensioned and in particular have different inner diameters. Such a gas inlet element 66 may be moved with respect to the mixing chamber 62, such that a selected one of the inlet openings 64, 64*a* can be brought in communication with the inner volume of the mixing chamber 62. For example, inlet opening 64 may be brought in communication with the inner volume instead of inlet opening 64*a*. Alternatively, one of the inlet openings 64, 64*a* may brought into communication with the inner volume in addition to the other one of the inlet openings 64, 64*a*.

FIG. 5 shows another exemplary embodiment of the gas inlet element 166 in a schematic view. For the sake of brevity, only differences to the exemplary embodiment of FIG. 4 are discussed.

The gas inlet element 166 of FIG. 5 has a circular cross-section and may be formed as a round disk or a cylinder. The gas inlet element 166 may be rotatable or revolvable around an axis, for example a central axis of the gas inlet element 166, in order to bring selected inlet openings 164, 164*a*, 164*b*, 164*c* in communication with the inner volume of the mixing chamber 62. As shown in the exemplary embodiment of FIG. 5, the gas inlet element 166 comprises more than one and for example four inlet openings 164, 164*a*, 164, 164*c*, which are differently dimensioned. For example, in a clock-wise direction D of the circular gas inlet element 166, inner diameters of the inlet openings 164, 164*a*, 164, 164*c* may increase.

The dispensed material to be atomized may be atomized and for example vaporized in less than one second by the atomizing element 68 as shown in FIG. 3. Preparing for example heating the atomizing element 68 and blending the aerosols with gas, e.g. ambient air, to form the inhalant, typically adds less than 2 seconds to the atomization of the material, such that the whole atomizing and provision of the aerosols to be inhaled as inhalant takes no more than 2 seconds. Hence, the user can inhale the generated inhalant completely during one puff, which takes less than 3 seconds.

Preferably, the predetermined operation temperatures of the atomizing element 68 shown in FIG. 3 are constant but different in order to generate aerosols with different particle sizes and the gas dilution of the atomized particles is constant. In particular, the energy supply to the atomizing element 68 is varied and the airflow is not varied. Further, the predetermined quantity of the material, e.g. a liquid, to be dispensed and/or the predetermined operation temperature can be selectable by the user.

FIG. 6 shows a possible exemplary embodiment of the e-cigarette 10 with the aerosol generating component 40 according to any of the exemplary embodiments shown in FIGS. 2 and 3 in a schematic cross-sectional view. The liquid supply unit 60 and the optional liquid supply unit 60*a* may be provided between the liquid store 34 and/or the liquid store 34*a* as depicted in FIG. 3, and may replace the liquid conductors 50, 52, but are not shown in FIG. 6, for the sake of simplicity. Furthermore, at least one gas inlet element 66 shown in FIG. 4 and/or at least one gas inlet element 166 shown in FIG. 5 may be provided at at least one or at all of the air inlets 38 of the e-cigarette 10 depicted in FIG. 6, but are not shown in FIG. 6, for the sake of simplicity. The atomizing element 41 may or may not be placed in the mixing chamber 62. The mixing chamber 62 may be provided independent of the liquid supply units 60, 60*a*. Further elements of the embodiments shown in FIGS. 2 and 3 may optionally be provided, but are not shown, for the sake of simplicity.

FIG. 7 shows a possible embodiment of the method according to the invention in a schematic view as a flow chart. Reference signs of elements of the previous embodiments are used in the following, in order to be able to better describe the method, where applicable.

The method 90 for providing an inhalant to a user starts with a first method step 91. In the first method step 91, the user may begin to puff on the electronic smoking device 10 or may actuate a switch or button in order to activate the aerosol generating component 40.

After method step 91, method step 92 follows, in which a first aerosol with a first particle size is generate and mixed with a gas, e.g. air, in order to form an inhalant to be inhaled by the user. During the second method step 92, a liquids may be atomized with a first atomization rate, for example with the atomizing element 41. Alternatively or additionally, the aerosol, e.g. the atomized liquid, may be diluted with the diluting gas in order to form the inhalant, wherein the amount of the diluting gas is set to a pre-determent value, e.g. by the air supply 46.

Due to the rate of atomization and/or the amount of diluting gas, the first aerosol is generated with the first particle size.

For example, the power used for atomizing the liquid can be set to a predetermined power in order to atomize the liquid with the predetermined rate. Alternatively or additionally, the mass of the liquid to the atomized, for example its flow rate towards the atomizer 26, can be set to a predetermined value, for example by the liquid supply unit 60, again, in order to generate the first aerosol with the first particle size.

In order to dilute the atomized liquid with the predetermined amount of the diluting gas, the diluting gas can be transported via a duct with a predetermined inner diameter and/or can be transported by a predefined pressure difference.

Method step 92 is followed by method step 93, in which the second aerosol with the second particle size is generated. Hence, the method steps 92 and 93 are consecutively performed, such that the first and the second aerosols are consecutively generated. Between the method steps 92 and 93, another method step 94 is performed, in which the rate of atomization and/or the amount of diluting gas used for diluting the atomized liquid is changed. The change of the operating parameters atomization rate or amount of diluting gas causes the change of the size of the particles generated.

For example, the power used for atomizing the liquid can be increased or decreased. Furthermore, the mass of the liquid to be atomized can be increased or decreased. Alternatively or additionally, the inner diameter of the duct used to transport the diluting gas can be changed, for example by adding a duct or by exchanging the duct. The inner diameter of the duct is preferably defined by the gas inlet element 66, 166 and in particular by the inlet openings 64, 64*a*, 164, 164*a*, 164*b*, 164*c*. Furthermore, the duct may comprise a variable inner diameter, which can be changed in method step 94. Further, in addition or as an alternative to the change of the inner diameter, the pressure difference causing the flow of the diluting gas can be changed, in order to increase or decrease the flow of the diluting gas.

The first aerosol and the second aerosol can be generated from identical liquids or from the same liquid. Such a liquid may comprise a nicotine product and a flavor product. Alternatively, the first aerosol can be generated from a first and the second aerosol can be generated from a second liquid, wherein the first liquid differs from the second liquid. For example, the first liquid is a nicotine product and the second liquid is a flavor product.

Method step 95 follows on method step 93. With method step 95, the method 90 for providing an inhalant to a user ends. For example, the user stops puffing or releases the button or switch, such that the aerosol generating component 40 stops generating the aerosol to be inhaled.

In the following, the aerosol generating component, the electronic smoking device and the method are further described in an exemplary manner.

According to one aspect of the present invention there is provided an aerosol generating component for an electronic smoking device. The aerosol generating component comprises an and preferably exactly or not more than one atomizer. The atomizer is adapted to consecutively generate two aerosols with different particle sizes. For example, the atomizer comprises one and preferably exactly or not more than one atomizer element, the atomizer element being adapted to consecutively generate two aerosols with different particle sizes. Furthermore, in accordance with another aspect of the present invention, there is provided an electronic smoking device comprising an aerosol generating component according to the invention. Moreover, in accordance with yet another aspect of the present invention, there is provided a method for generating an inhalant to a user. In order to generate the inhalant, a first aerosol with a first particle size and a second aerosol with a second particle size are consecutively generated. The first particle size differs from the second particle size.

An advantage of the above aerosol generating component may be that the particle size can be preselected for chosen materials to be inhaled, such that the materials can be transported to desired locations within the respiratory system of the user of the smoking device.

For example, in case a first of the materials to be inhaled is a flavor product, the particle size of the flavor product in the aerosol can be chosen to be large. For example, the size of the large particles may be larger that a size of smaller particles of the other aerosol. The size difference of small and larger particles such that the size of large particles corresponds to a percentage of the size of the smaller particles, wherein the size difference may be selected from a rage that can be formed by selecting any percentage listed in the following as upper and lower values of that range, namely 110%, 120%, 125%, 130%, 150%, 175%, 200%, 250%, 500%, 750% and 1000%. This, the size of the larger particles may correspond to the size of the smaller particles multiplied by and of the above mentioned percentages or a value therebetween. For example, larger particle may be larger than 5 μm, such that the first material is more likely to be deposited higher in the respiratory track (such as in the buccal and nasal cavity where the taste and smell receptors are located) and can improve the user's taste experience more efficiently. The second material to be inhaled may be a nicotine product, for example a product that contains a certain amount of nicotine, wherein the size of the particles of the second product in the aerosols may be smaller than the particle size of the first product and for example between 1 and 3 μm, such that the nicotine containing particles are more likely to be deposited in the lower respiratory tract where the transfer to the bloodstream is most efficient. For example, in case the size of the smaller particles is 1 μm, a larger particle with a size of 5 μm has a size that corresponds to 600% of the size of the smaller particles.

Hence, less nicotine needs to be inhaled by the user in order to achieve a desired effect, compared to a traditional electronic cigarette where the particle size is not optimized for nicotine transfer to the blood. Yet, the user's taste experience is not affected by the effective transport of the nicotine particles.

The particle size preferably is a typical particle size of the material to be inhaled in the aerosol. For example, the particle size may be the mean particle size of the particles of one of the products to be inhaled, typically about 1 to 15 μm. Alternatively, the particle size distribution may have its maximum value at the typical particle size of the particles of one of the products to be inhaled. The particle sizes may be specified as mass median aerodynamic diameter.

The solutions described in the following can be combined as desired and further improved by the further following embodiments that are advantageous on their own, in each case and unless stated to the contrary.

Preferably, the aerosol generating component is adapted to consecutively generate the two aerosols with different particle sizes within one atomization cycle. An atomization cycle may be a continuous cycle, in which the materials for the two aerosols are formed and during which the atomizer and in particular of the atomizer element is continuously operated. Alternatively, the atomization cycle may be a cycle that extends over more than one operation cycle of atomizer and in particular of the atomizer element, wherein the operation cycles of the atomizer and in particular of the atomizer element may be performed directly after each other of with a time gap therebetween.

When the electronic smoking device according to the invention is in use, a user sucks on a mouthpiece portion of the electronic smoking device. One sucking cycle may correspond to one puff the user takes from the electronic smoking device. During the puff, the aerosol generating component performs one and preferably exactly and not more than one atomization cycle, such that the inhalant consecutively comprises the two aerosols and can be readily consumed by the user with one puff. The duration of a puff may be up to 5 and preferably up to 3 seconds. Within the puff, the aerosols with the different particle sizes are generated by supplying the liquids to be atomized, atomizing the liquids and mixing the liquids with gas, preferably air, to form the inhalant. Hence, the user of the aerosol generating component can inhale both of the aerosols within the one puff.

In order generate two aerosols with different particle sizes, the aerosol generating component may be adapted to change the rate of atomization of a liquid from which the aerosol is formed from a first predetermined rate to a second predetermined rate, such that the aerosol generating component is adapted to consecutively use two different predetermined atomization rates. Hence, when performing the method, the rate of atomization may be changed and two different predetermined atomization rates may be consecutively applied in order to consecutively generate the differently sized particles.

The aerosol generating component may be adapted to change the rate of atomization by changing operation energy from a first predetermined energy to a second predetermined energy, i.e. by consecutively using different predetermined operation energies provided to the atomizer. Thus, according to the method, the power used for atomizing liquids to form the respective aerosols may be changed from a first predetermined power to a second predetermined power in order to generate the differently sized particles. The first predetermined power may be utilized to generate first rate of atomization and, therefore, the first particle size, and the second predetermined power may be utilized to generate the second rate of atomization and, therefore, the second particle size. Varying the rate of atomization by varying the operation energy provided to the atomizer or the power used for atomizing liquids can be easily accomplished by electronics.

Alternatively or additionally, the aerosol generating component can be adapted to change the mass of liquid to be atomized and to be fed to the atomizer from a first predetermined mass to a second predetermined mass in order to change the rate of atomization, such that the aerosol generating component is adapted to consecutively supply different predetermined amounts of liquid to the atomizer. Thus, the mass of the liquids to be atomized to form the respective aerosols may be changed and different predetermined quantities may be consecutively provided in order to generate the differently sized particles when conducting the method.

A higher mass of the liquid has a higher thermal mass than a mass of the same liquid that is less than the higher mass. Hence, with a higher mass of liquid, a higher rate of atomization can be achieved compared to a lower mass of liquid. The mass of liquid is preferably supplied to the atomizer and atomized within the puff. For example, the mass of liquid supplied may be changed during the puff from the first predetermined mass to the second predetermined mass, such that in a first time period, the aerosol with the first particle size, and in a second time period, the aerosol with the second particle size can be generated. In particular, the flow of liquid to the atomizer may be changed, such that the aerosol with the first particle size is generated with a first flow and the aerosol with the second particle site is generated with a second flow of liquid to the atomizer, wherein the flows differ from each other.

The aerosols may be diluted with a diluting gas, for example air, in order to form the inhalant. In addition or as an alternative to changing the rate of atomization, the amount of gas used to dilute the aerosols, i.e. the atomized liquids, may be changed from a first predetermined amount to a second predetermined amount in order to consecutively generate the differently sized particles. Hence, different flows, amounts or quantities of gas can be consecutively used for the dilution and the aerosol generating component may be is adapted to change the amount of diluting gas, e.g. air, led to the atomizer from a first predetermined amount to a second predetermined amount in order generate two aerosols with different particle sizes. Thus, different flows, amounts or quantities of gas can be consecutively used for the dilution.

A high amount of diluting gas may result in a high dilution, such that the particles interact less with each other and the average particle size remains to be low compared to a lower amount of diluting gas. Further, a fast stream of diluting gas may result in a turbulent gas stream, which results in high interactivity of the particles, which results in larger particles compared to less or not at all turbulent diluting gas streams.

In order to change the amount of a diluting gas, an inner diameter of a duct transporting the diluting gas may be changed from a first predetermined diameter to a second predetermined diameter in order to change the amount of gas used to dilute the aerosol. Thus, the aerosol generating component is preferably adapted to change a pressure difference that causes the diluting gas to flow to the atomizer from a first predetermined difference to a second predetermined difference.

For changing the inner diameter of the duct used for transporting the diluting gas, the aerosol generating component may comprise two ducts with different inner diameters, the ducts being alternatingly connectable to the atomizer. Alternatively, the aerosol generating component may be provided with one duct, only, whose inner diameter is changeable. Due to the different inner diameters used to transport the diluting gas, the flow rate may be changed even with a constant pressure difference that transports the diluting gas. Furthermore, the Reynolds-number of the diluting gas stream flowing to the atomizer may change with the inner diameter or with other properties or parameters of the gas stream, such that the diluting gas stream may change from a less or not at all turbulent gas stream to a more turbulent or turbulent gas stream.

Furthermore, the pressure difference transporting diluting gas may be changed from a first predetermined difference to a second predetermined difference in order to change the amount of gas used to dilute the aerosol. Thus, the aerosol generating component may be adapted to change a pressure difference that causes the diluting gas to flow to the atomizer from the first predetermined difference to the second predetermined difference. Therefore, two different predetermined pressure differences may be applied consecutively. In order to change the pressure difference that causes the flow of diluting gas, valves and/or openings with different or variable inner diameters may be provided, through which the diluting gas flows when the user sucks on the mouthpiece portion. Other element for changing the pressure difference from the first to the second difference may be provided alternatively or in addition.

Both of the aerosols may be generated with an aerosol generating component or with an electronic smoking device according to any embodiment of the above description. Hence, the aerosol generating component or the electronic smoking device according may be adapted to perform the method of the invention according to any, selected or all embodiments.

The particle size is preferably controlled by the rate of atomization and/or by the diluting rate. The rate of atomization may be controlled by electric current applied to the atomizing element and/or by the mass the liquid applied to the atomizing element. The dilution rate may be controlled by the amount of air passing through or along the atomizing element during an atomizing cycle.

With fixed atomizing conditions and fixed liquid injection mass, the practical size is preferably controlled by the volume of diluting gas, with which the atomized liquid is diluted. The dilution lowers the probability of particles hitting each other and, thereby, forming larger particles. Increasing dilution decreases the rate of change in particle number and diameter.

With a fixed airflow, a higher rate of atomization can generate larger particles. Rapid heating may cause nucleation points to form, and as these gaseous bubbles escape the liquid, they weaken the intermolecular forces that are preventing other liquid molecules from escaping into the gaseous phase, i.e. reduce the enthalpy of atomization. The rate of atomization can be controlled by the liquid mass, the thermal mass of the atomizer, e.g. a heating coil, and electric current applied.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS

D clock-wise direction
P flow path
10 e-cigarette/electronic smoking device
12 main body
14 mouthpiece portion
16 end cap
18 battery
20 light emitting diode (LED)
22 control electronics
24 airflow sensor
26 atomizer
28 heating coil
30 wick
32 central passage
34, 34*a* liquid store
36 air inhalation port
38 air inlets
40 aerosol generating component
41 atomizing element
42 control unit
44, 44*a* signal conductor
46 air supply control unit
48 signal conductor
50, 52 liquid conductors
54 input side
56 output side
58 adapter 60, 60a liquid supply unit
62 mixing chamber
64, 64a inlet opening
66 gas inlet element
70 control contact
72 temperature sensor
74 signal contact
76, 76a nozzle
78, 78a value
80, 80a control contact
82, 82a pump
84, 84a control contact
90 method
91 start/puff or push button
92 generate first aerosol
93 generate second aerosol
94 change parameter
95 end
164-164c inlet opening
166 gas inlet element

The invention claimed is:

1. An aerosol generating component for an electronic smoking device comprising:
an atomizer adapted to consecutively generate two aerosols with different particle sizes, wherein the aerosol generating component is adapted to change the amount of a diluting gas led to the atomizer from a first predetermined amount to a second predetermined amount in order generate the two aerosols with different particle sizes, and wherein the aerosol generating component comprises two ducts that transport the diluting gas, the two ducts having different inner diameters, the ducts being alternatingly connectable to the atomizer.

2. The aerosol generating component according to claim 1, wherein the atomizer comprises one atomizer element that is adapted to consecutively generate two aerosols with different particle sizes.

3. The aerosol generating component according to claim 1, wherein the aerosol generating component is adapted to consecutively generate two aerosols with different particle sizes within one atomization cycle.

4. The aerosol generating component according to claim 1, wherein the aerosol generating component is adapted to change the rate of atomization of a liquid from which the aerosol is formed from a first predetermined rate to a second predetermined rate in order generate two aerosols with different particle sizes.

5. The aerosol generating component according to claim 4, wherein the aerosol generating component is adapted to change operation energy provided to the atomizer from a first predetermined energy to a second predetermined energy in order to change the rate of atomization, wherein higher energy leads to higher rate of atomization and the larger particle size.

6. The aerosol generating component according to claim 4, wherein the aerosol generating component is adapted to change the mass of liquid to be atomized and to be fed to the atomizer from a first predetermined mass to a second predetermined mass in order to change the rate of atomization.

7. The aerosol generating component according to claim 1, wherein the aerosol generating component is adapted to change a pressure difference that causes the diluting gas to flow to the atomizer from a first predetermined difference to a second predetermined difference.

8. An electronic smoking device comprising an aerosol generating component according to claim 1.

9. The electronic smoking device according to claim 8, wherein the aerosol generating component is adapted to consecutively generate two aerosols with different particle sizes within one puff.

10. The aerosol generating component of claim 1 wherein each of the two ducts has a fixed inner diameter.

11. A method for providing an inhalant to a user,
consecutively generating wherein a first aerosol with a first particle size and a second aerosol with a second particle size, the first particle size differing from the second particle size;
diluting the aerosols with a diluting gas to form the inhalant and the amount of the diluting gas used to dilute the aerosols is changed from a first predetermined amount to a second predetermined amount to generate the first and second particle sizes; and
changing an inner diameter of a duct transporting the diluting gas from a first predetermined diameter to a second predetermined diameter in order to change the amount of gas used to dilute the aerosol.

12. The method according to claim 11, wherein the rate of atomization is changed from a first predetermined rate to a second predetermined rate in order to generate the differently sized particles.

13. The method according to claim 11, wherein the power used for atomizing is changed from a first predetermined power to a second predetermined power in